United States Patent
Bell

(10) Patent No.: US 6,248,099 B1
(45) Date of Patent: Jun. 19, 2001

(54) DISPOSABLE TRACHEOSTOMY INNER CANNULA CONNECTOR

(75) Inventor: Craig J. Bell, E. Swanzey, NH (US)

(73) Assignee: Medcare Medical Group, Inc., E. Swanzey, NH (US)

( * ) Notice: Subject to any disclaimer, the term of this patent is extended or adjusted under 35 U.S.C. 154(b) by 0 days.

(21) Appl. No.: 09/078,868

(22) Filed: May 14, 1998

(51) Int. Cl.⁷ .................................................. A61M 25/16
(52) U.S. Cl. .......................... 604/533; 604/264; 604/535
(58) Field of Search .................................. 604/523, 533, 604/534, 535, 264, 405; 128/200.26, 207.15

(56) References Cited

U.S. PATENT DOCUMENTS

| | | |
|---|---|---|
| 3,088,466 | 5/1963 | Nichols . |
| 3,169,529 * | 2/1965 | Koenig ................................. 128/351 |
| 3,659,612 | 5/1972 | Shiley et al. . |
| 3,693,634 | 9/1972 | Gilbert . |
| 4,009,720 | 3/1977 | Crandall . |
| 4,033,353 * | 7/1977 | La Rosa ............................... 128/351 |
| 4,304,228 * | 12/1981 | Depel .............................. 128/200.26 |
| 4,315,505 | 2/1982 | Crandall et al. . |
| 4,817,598 | 4/1989 | LaBombard . |
| 5,149,330 * | 9/1992 | Brightbill ............................. 604/280 |
| 5,357,952 | 10/1994 | Schuster et al. . |
| 5,390,669 | 2/1995 | Stuart et al. . |
| 5,460,176 | 10/1995 | Frigger . |

* cited by examiner

*Primary Examiner*—Richard K. Seidel
*Assistant Examiner*—Michael Hayes
(74) *Attorney, Agent, or Firm*—Davis & Bujold, P.L.L.C.

(57) ABSTRACT

A disposable tracheostomy inner cannula connector that is compatible with prior art disposable inner cannula tracheostomy tube systems. The connector has an annular ring at a proximal end thereof which allows the inner cannula to snap in the connector and thereby secure the inner cannula in place. A locking mechanism of the connector, located at the distal end, permanently affixes the outer cannula to the connector.

20 Claims, 4 Drawing Sheets

DISPOSABLE TRACHEOSTOMY INNER CANNULA CONNECTOR

FIELD OF THE INVENTION

The present device relates to an improvement concerning tracheostomy tubes. The tracheostomy tubes are generally comprised of an outer cannula and a disposable inner cannula.

BACKGROUND OF THE INVENTION

Tracheostomy tubes are used in the health care field to provide a bypass supply of air or gases to a patient having an obstruction of the larynx or pharynx and who is thus no longer able to breath through the normal route. Tracheostomy tubes are also placed in patients who, because of injury or disease, cannot breath on their own. These patients are chronically dependant on mechanical ventilation and the long-term artificial airway of choice is the tracheostomy tube.

An incision is made by the doctor below the obstruction and the tube inserted. The tube then acts as a gateway, allowing the patient to breath normally, the proximal end of the tube remaining stationary outside the trachea.

The tracheostomy tube has a tendency to become either partially or completely obstructed, over time, by the accumulation of mucus or phlegm. To resolve this problem, a system where two cannulas are placed one inside the other has been developed, which allows for the removal of the inner cannula to facilitate cleaning while still maintaining the outer cannula in the patient's trachea, U.S. Pat. No. 3,693,634 to Shiley/Mallinckrodt. Problems may occur due to accidental disconnection of the inner and outer cannulas of the tracheostomy tube, thereby allowing for spillage and/or slippage between the two. This slippage may cause a disconnection a ventilator resulting in the death of the patient.

There are several devices which contain a means of connecting the inner cannula to the outer cannula and the outer cannula to the ventilation system. These include, but are not limited to, U.S. Pat. No. 3,659,612 to Shiley et al., U.S. Pat. No. 4,009,720 to Crandall, et al. and U.S. Pat. No. 3,088,466 to Nichols. Inherent in these tracheostomy tube designs is the fact that two separate connectors are required. This means that there are two disconnection points which reduces the safety of the system, the accidental disconnection of the inner cannula with the ventilation system being increased. In addition, an air tight seal must be present between the inner and outer cannula to ensure that the respiration pressure from an artificial ventilation system is maintained and leakage does not occur. Another disadvantage is that while the inner cannula is removed, the ventilator cannot be connected to the tracheostomy tube, if needed.

U.S. Pat. No. 4,817,598 to LaBombard discloses a disposable inner cannula tracheostomy tube with a ventilator connector that is permanently fixed to the outer cannula. The proximal end of the inner cannula fits into the inner diameter of the connector and is fixed with opposing ribs and grooves that create a "SNAP" connection. The inner cannula has a proximal ring that is connected by a hinge to provide a gripping surface for removal of the inner cannula from the outer cannula.

The major problem with both the LaBombard and the Shiley devices is that they are not compatible with one another. This has created a strain on consumers in the disposable inner cannula market. What is needed is a connector device which can be used in conjunction with all the available disposable inner cannulas on the market to allow interchangability of the inner cannula with the tracheostomy tube and increase its safety. Such a connector will allow the care-giver and patient to take advantage of the product benefits of the Shiley device as well as those of the LaBombard tracheostomy tube.

SUMMARY OF THE INVENTION

Wherefore, it is an object of the present invention to overcome the aforementioned problems and drawbacks associated with the prior art designs.

The device, according to the present invention, relates to tracheostomy tubes, in particular, those that are disposable and composed of an outer cannula and a disposable inner cannula. The device will allow for the interchangability between various manufacturers as well as allowing for the permanent attachment of the ventilator connector thus increasing safety to the patient.

In a preferred embodiment of the invention, the connector, used to attach the outer cannula with the inner cannula, comprises: a) a locking means; b) a standard taper; c) an annular ring; and d) securing means. The connector may be constructed from material such as polypropylene, polyethylene, polycarbonate, polyvinyl chloride or another material that is capable of maintaining rigidity during the connector's attachment. The locking means of the device projects outward from the connector's distal end and has a lip to facilitate the connector's attachment to an outer cannula. A standard 1 in 40 taper is provided on the exterior surface of the connector with a nominal outer diameter of 15 mm throughout the length of the connector. In addition, there is a compression rib attached to the distal portion of the locking means which encompasses the connector to compensate for variances in the proximal end of the connector portion of the disposable inner cannula. The annular ring has a slightly smaller diameter than the diameter of the annular protrusion of the inner cannula to provide an interference fit therebetween.

In another preferred embodiment, the connector is described through its use. Its use being a method of permanently attaching a connector to a tracheostomy outer cannula comprising a series of steps. First, a connector with an elongate housing must be provided, having a through bore extending longitudinally completely through the elongate housing. Then an inwardly facing annular ring must be located within the through bore, adjacent one end thereof, for facilitating engagement with a recess of an inner cannula. Finally, a locking mechanism is required on the connector for supporting the outer cannula in a locking engagement with the connector.

The present invention relates to a connector for interconnecting an inner cannula with an outer cannula, the connector comprising: an elongate housing defining a through bore extending longitudinally completely therethrough; an inwardly facing annular ring being located within the through bore, adjacent one end thereof, for facilitating engagement with a recess of an inner cannula; and the connector supporting a locking mechanism for facilitating a locking engagement with an outer cannula.

DESCRIPTION OF THE DRAWINGS

The device will now be described by way of example, with reference to the accompanying drawings in which.

DETAILED DESCRIPTION OF THE INVENTION

The following description is in no way meant to limit the scope of the connector device in size, shape, materials used in its construction, or in the orientation of the components. The 15 mm connector 2, according to the present invention, is envisioned being made from a material including, but not limited to, polypropylene, polyethylene, polycarbonate, polyvinyl chloride or other similar materials capable of maintaining rigidity to facilitate remaining permanently attached to the outer cannula 38 of a disposable tracheostomy tube 3 once "SNAPPED" in position. The 15 mm connector 2 typically remains located on the tracheostomy tube 3 for the life of the tracheostomy tube 3 which, in most applications, is approximately thirty (30) days.

Figure 1B:
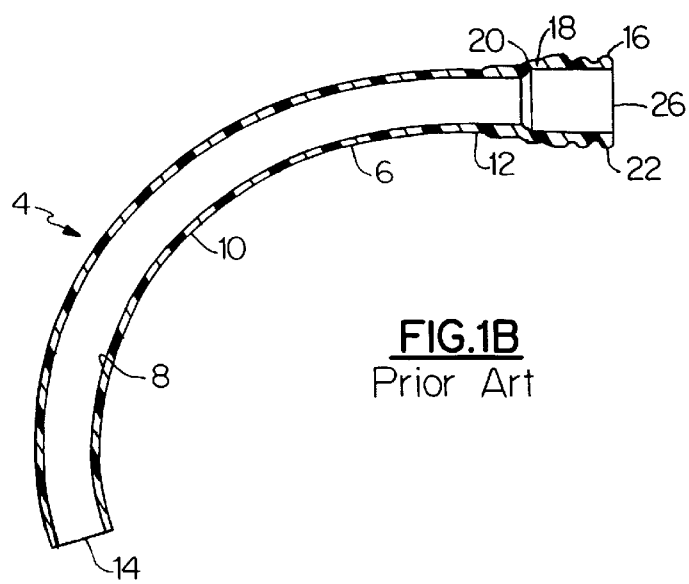
FIG. 1B is a diagrammatic cross-sectional view of the prior art inner cannula of FIG. 1A.
Figure 1A:
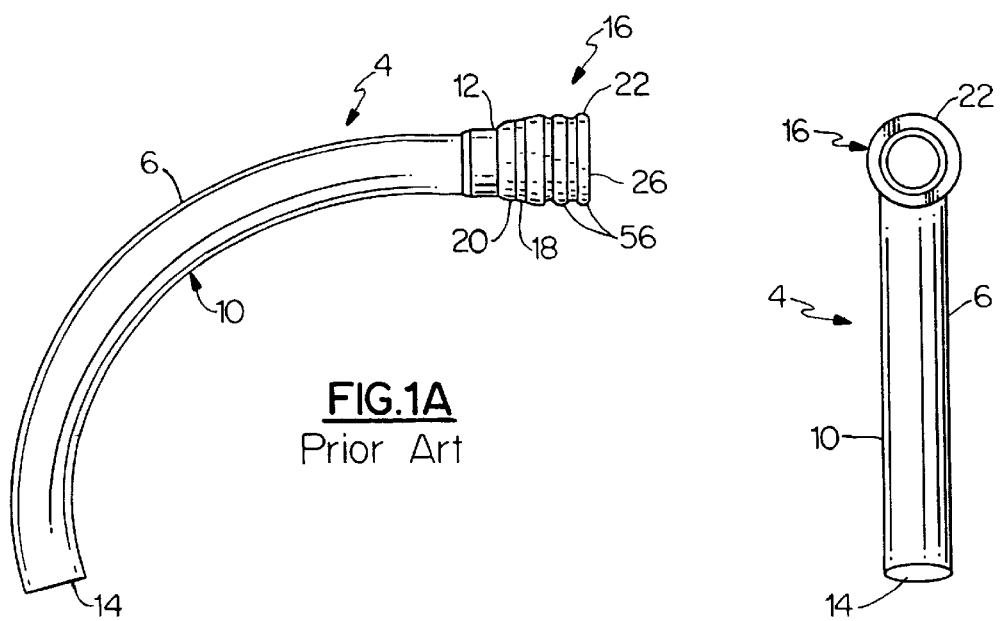
FIG. 1A is a diagrammatic side elevational view of a prior art inner cannula.
Figure 1C:
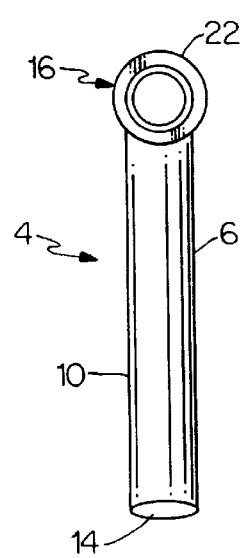
FIG. 1C is a diagrammatic front elevational view of the prior art inner cannula of FIG. 1A.
Figure 2:
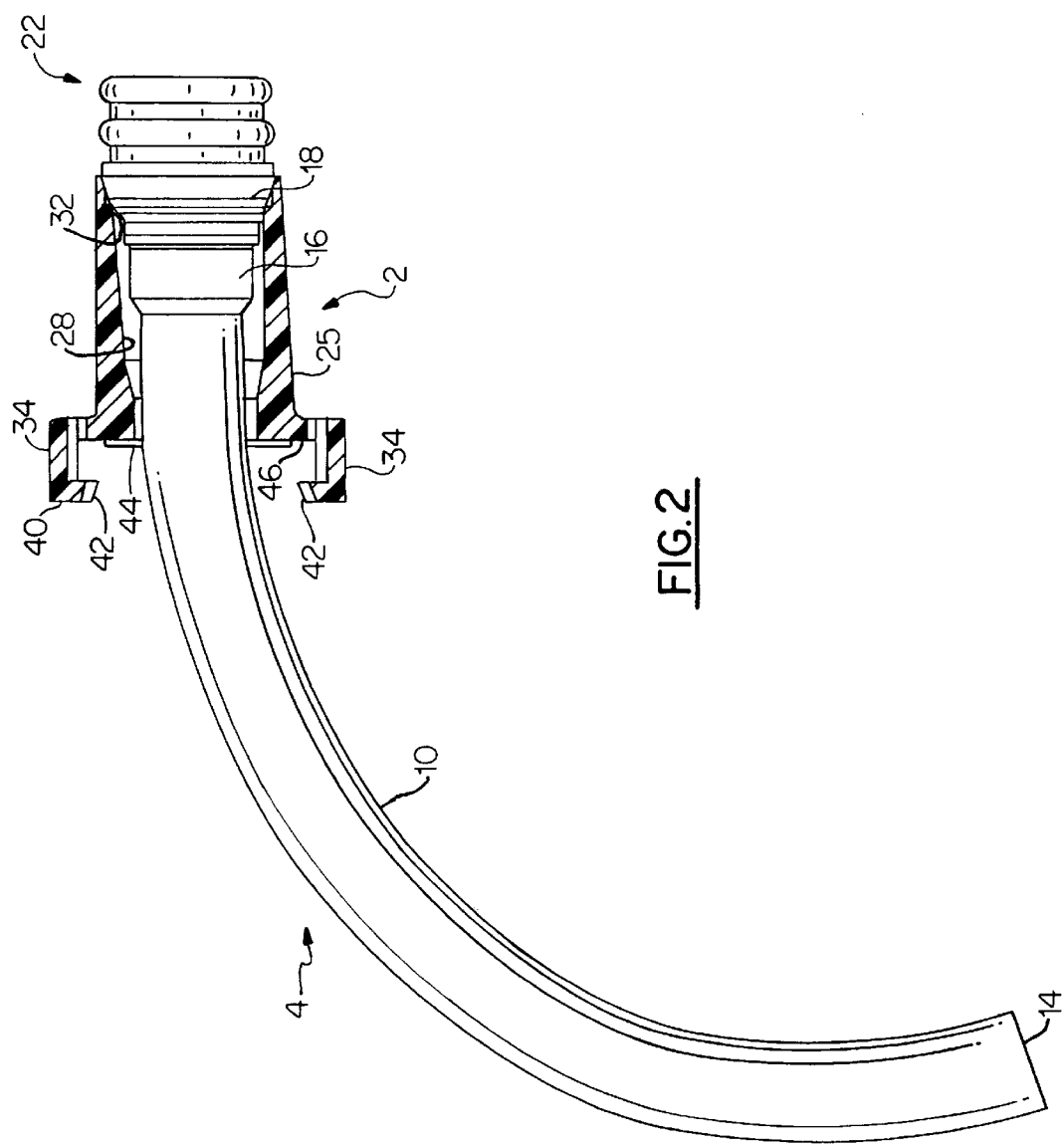
FIG. 2 is a partial diagrammatic cross-sectional view of the prior art inner cannula of FIG. 1A in combination with a 15 mm connector according to the present invention.
Figure 3B:
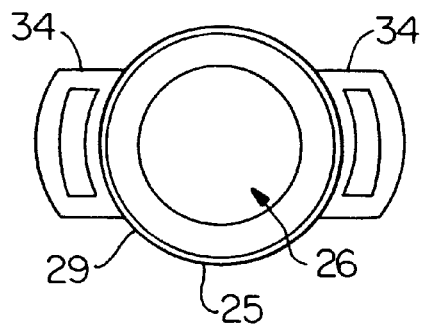
FIG. 3B is a diagrammatic top elevational view of the 15 mm connector of FIG. 3A.
Figure 3A:
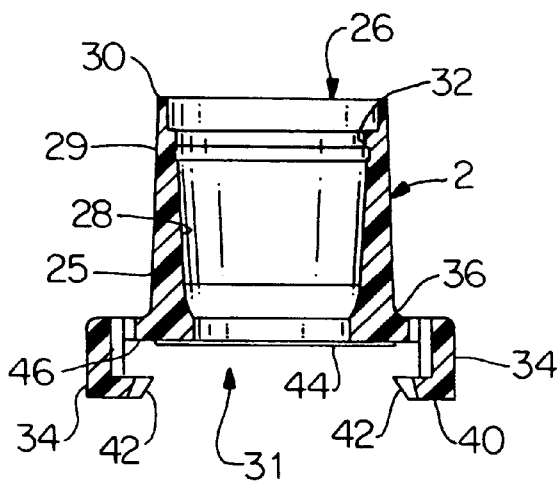
FIG. 3A is a diagrammatic transverse cross-sectional view of the 15 mm connector according to the present invention.
Figure 3D:
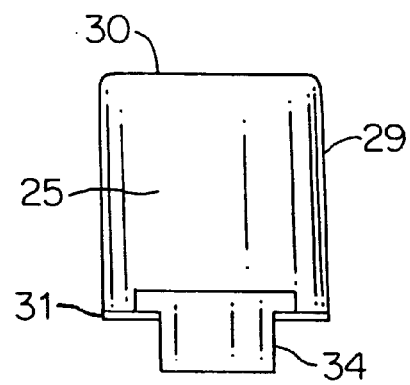
FIG. 3D is a diagrammatic side elevational view of the 15 mm connector of FIG. 3A.
Figure 3C:
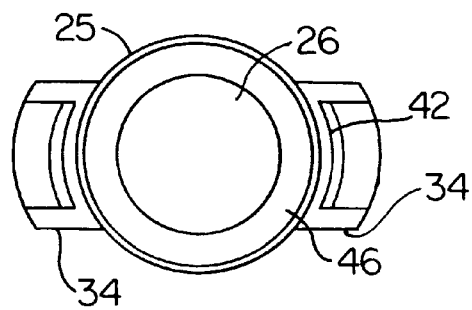
FIG. 3C is a diagrammatic bottom elevational view of the 15 mm connector of FIG. 3A.

Turning first to FIGS. 1A–1C, a brief description concerning a known prior art inner cannula 4 will now be provided. As can be seen in these three Figures, the inner cannula 4 comprises an elongate hollow tube 6 having an interior surface 8 and an exterior surface 10 and a length of about between three and six inches. The elongate hollow tube 6 has a proximal end 12 and a distal end 14. The proximal end 12 of the elongate tube 4 has an enlarged head 16 formed integrally therewith to facilitate securement of the inner cannula 4 to the 15 mm connector 2, according to the present invention, and a further discussion concerning the same will follow.

The enlarged head 16 has an exterior annular recess 18 formed therein which is located adjacent an exterior annular protrusion 20. The purpose of these two components will become apparent from the following discussion of the present invention. The enlarged head 16 has a handle grip 22 which separates both the annular recess 18 and the annular protrusion 20 from a remainder of the proximal end 26 of the enlarged head 16. The handle grip 22 facilitates removal of the inner cannula 4 from the tracheostomy tube 3, by a user, and a further discussion concerning the same will be provided below.

Turning now to FIGS. 2 and 3A–3D, a detailed description concerning the 15 mm connector 2, according to the present invention, and its interaction with the inner cannula 4 and the outer cannula 38 will now be provided. As can be seen in these five Figures, the 15 mm connector 2 has an elongate housing 25 which is provided with a longitudinal through bore 26 extending completely therethrough. The through bore 26 has an interior surface 28 and an exterior surface 29. The exterior surface 29 is provided with a slight (standard) taper, e.g. a 1 in 40 slope, to facilitate connection to a ventilator system in a conventional manner. The proximal end 30 of the interior surface 28 of the 15 mm connector 2 has an inwardly facing annular ring 32 which is located to engage with and lockingly retain the annular recess 18 of the inner canula 4.

Such locking retainment is achieved by passing the inner canula 4, the distal end 14 first, in the through bore 26 until the protrusion 20 contacts the inwardly facing annular ring 32. Further insertion of the inner canula 4, in the same insertion direction, causes one or both of the annular ring 32 and the annular protrusion 20 to be slightly compressed as the annular ring 32 slides over the annular protrusion 20 and thereafter the annular ring 32 is received, e.g. "SNAPPED", and retained by the annular recess 18 to lock the position of the inner canula 4 relative to the 15 mm connector 2.

Figure 4:
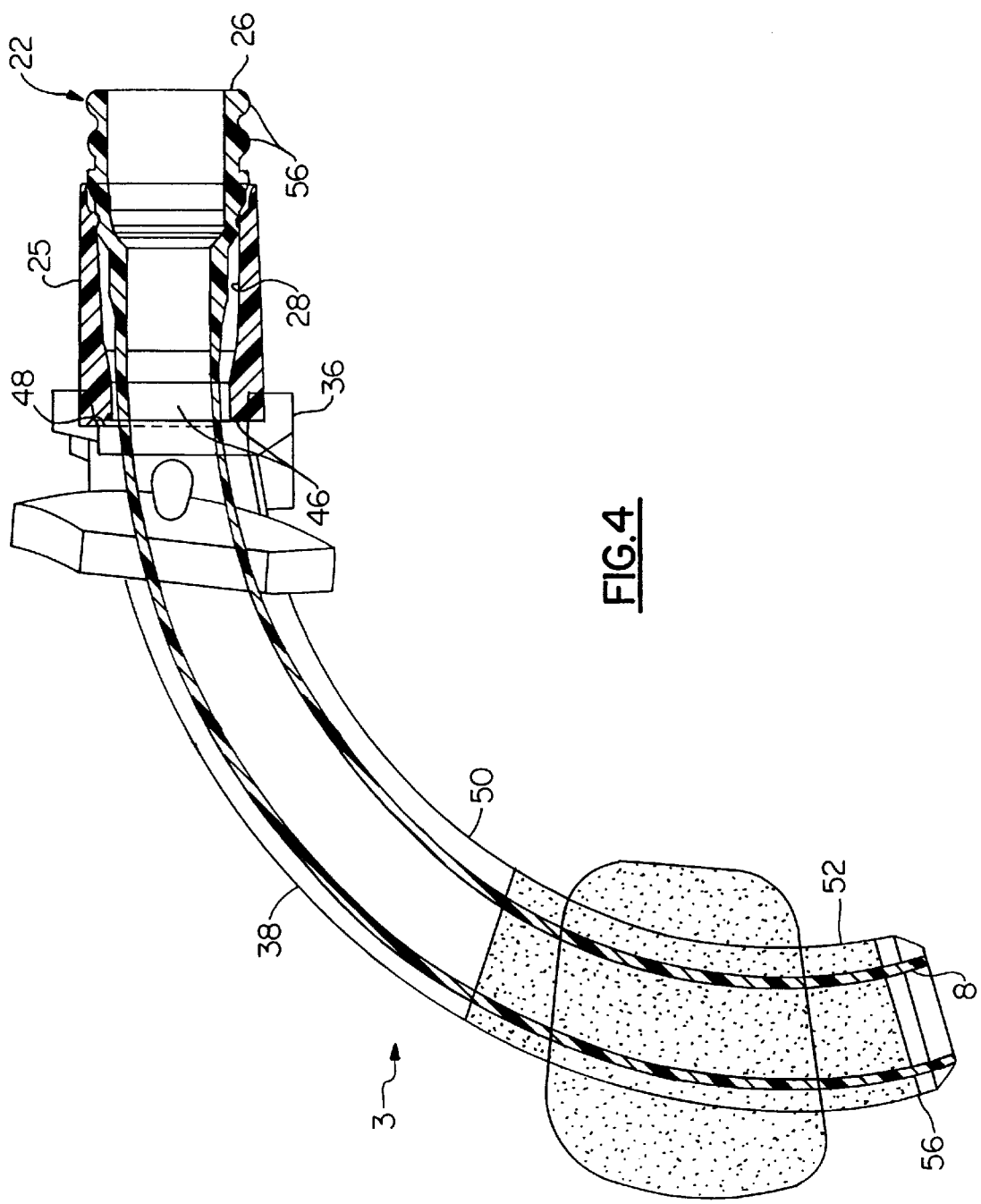
FIG. 4 is a partial diagrammatic cross-sectional view of the prior art inner cannula of FIG. 1A located within a prior art outer cannula both coupled to the 15 mm connector according to the present invention.

The distal end 31 of the 15 mm connector 2 supports a pair of opposed locking mechanisms or flexible arms 34 which are located to engage with an annular flange 36 provided on the proximal end of the hollow outer canula 38 (FIG. 4). The opposed flexible arms 34 have a substantially U-shaped longitudinal cross-section (see FIG. 3A). The free end 40 of each flexible arm 34 is provided with a chamfer 42 to facilitate receiving of the annular flange 36 of the outer cannula 38 and maintain a permanent locking engagement between the outer cannula 38 and the 15 mm connector 2.

A thin, flat annular seal or gasket 44, such as an lastomeric O-ring, is provided between a flat planar end ace 46 of the 15 mm connector 2 and a mating flat planar end face 48 located on the proximal end of the outer annula 38, e.g. on the annular flange 36. The annular gasket 44 compensates for manufacturing and/or tolerance errors of these two components to facilitate a fluid tight sealing engagement therebetween.

The flexible arms 34 are sized so that when the annular flange 36 of the outer cannula 38, as well as the annular gasket 44, are accommodated between the U-shaped transverse cross-section of the flexible arms 34, the annular flange 36 and the annular gasket 44 are compressed somewhat against the opposed end faces 46 and 48 to provide a fluid tight seal between the outer cannula 38 and the 15 mm connector 2.

As can be seen in FIG. 4, the outer cannula 38 also comprises an elongate hollow tube 50 having an interior surface (not shown in detail) and an exterior surface 52. The elongate hollow tube 50 also has a proximal end 54 and a distal end (not shown in detail). The elongate hollow tube 50 is sized to receive the inner cannula 4 therein, with sufficient clearance between the two cannulas 4, 38, to facilitate easy relative movement therebetween.

The connection between the inner cannula 4 and the 15 mm connector 2 is maintained for the life of the inner cannula 4 which, on average, is about twenty-four (24) hours or so. To remove and/or replace the inner cannula 4, a user firmly grasps the exposed handling grip 22 of the inner cannula 4, e.g. two or more exposed ribs 56 facilitate such grasping, and pulls the inner cannula 4 with one hand while stabilizing a remainder of the tracheostomy tube 3 with the other hand. Such pulling action causes one or both of the annular ring 32 and the annular protrusion 20 to be slightly compressed, as the annular ring 32 once again slides over the annular protrusion 20, and is released from the annular recess 18 to "unlock" the inner cannula 4 from the 15 mm connector 2. Thereafter, the inner cannula 4 can be completely removed from the 15 mm connector 2 and a new inner cannula 4 can be inserted in place thereof in the previously discussed manner. During this replacement procedure, as well as during the entire life of the tracheostomy tube 3, the 15 mm connector 2 remains attached to the tracheostomy tube 3—on average the life of the tracheostomy tube 3 is about thirty (30) days.

FIG. 4 illustrates a diagrammatic cross sectional view of the Shiley/Mallinckrodt tracheostomy tube 3 showing the inner cannula 4 located within the outer cannula 38 with the 15 mm connector 2, according to the present invention, interconnecting both components with one another.

It is to be appreciated that the locking mechanism 34 is sized to be compatible with the proximal end of the prior art Shiley/Mallinckrodt tracheostomy tube 3. The annular ring 32 of the 15 mm connector 2 is also compatible with a prior art connector of the SIMS tracheostomy tube, which is not shown.

Since certain changes may be made in the above described, without departing from the spirit and scope of the invention herein involved, it is intended that all of the subject matter of the above description or shown in the accompanying drawings shall be interpreted merely as examples illustrating the inventive concept herein and shall not be construed as limiting the invention.

Wherefore, I claim:

1. A connector, for interconnecting an inner cannula with an outer cannula, the connector comprising:

an elongate housing having a distal end and a proximal end, the elongate housing having a through bore extending longitudinally completely there through from the distal end to the proximal end, and the through bore being sized to receive an inner cannula therein and tapering from the proximal end toward the distal end such that the proximal end is wider than the distal end;

an inwardly facing annular ring being located within the through bore of the elongate housing, adjacent the proximal end and remote from the distal end, for facilitating releasable engagement with an annular recess formed in an enlarged head of an inner cannula with a handle grip of the enlarged head of the inner cannula protruding out from the proximal end of the elongate housing to facilitate removal of the inner cannula from the connector when replacement of the inner cannula is required; and the connector supporting a locking mechanism, adjacent the distal end, for facilitating a locking engagement with an outer cannula, the locking mechanism comprising a pair of opposed arms located to engage with and retain the annular flange of the outer cannula whereby the connector can remain continuously engaged with an outer flange of an outer cannula even when an inner cannula is removed from the connector, by a user grasping an exposed portion of an enlarged head of an inner cannula, to replace the inner cannula.

2. The connector according to claim 1 in combination with an inner cannula and an outer cannula:

the inner cannula has a distal end and a proximal end, the proximal end of the inner cannula supports an enlarged head, the enlarged head has an annular protrusion located adjacent the annular recess and the annular recess is sized to intimately receive and engage with the inwardly facing annular ring to provide a releaseable locking engagement between the connector and the inner cannula; and the outer cannula has a distal end and a proximal end, and the proximal end of the outer cannula has an annular flange which is sized to be received by the locking mechanism of the connector to facilitate a substantially permanent engagement between the connector and the outer cannula.

3. The connector according to claim 2, wherein the locking mechanism comprises a pair of opposed arms which each have a chamfered surface to facilitate receiving the annular flange of the outer cannula member to facilitate a secure locking engagement therewith.

4. The connector according to claim 2 wherein an annular gasket is located between the distal end of the connector and the proximal end of the outer cannula to provide a sealing engagement therebetween.

5. The connector according to claim 2, wherein the connector is made from a material selected from the group comprising polypropylene, polyethylene, polycarbonate, and polyvinyl chloride.

6. The connector according to claim 2, wherein the annular ring has a slightly smaller diameter than the diameter of an annular protrusion of the inner cannula to provide an interference fit therebetween.

7. The connector according to claim 2, wherein an exterior surface of the connector has a taper to facilitate engagement with a ventilator system.

8. The connector according to claim 2, wherein the enlarged head is integrally formed with a remainder of the inner cannula.

9. A connector in combination with an inner cannula and an outer cannula:

the inner cannula comprising an elongate hollow tube and having an enlarged head, attached to one end of the elongate tube, with an annular recess being formed on the enlarged head, the enlarged head of the inner cannula has a handle grip, located adjacent the proximal end, to facilitate grasping and removal of the inner cannula from the connector;

the outer cannula comprising an elongate hollow tube and having a distal end and a proximal end, the proximal end of the outer cannula having an annular flange, and the elongate hollow tube of the outer cannula being sized to receive the inner cannula therein; and the connector comprising an elongate housing having a distal end and a proximal end and having a through bore extending longitudinally completely there through from the distal end to the proximal end; the through bore being sized to receive the enlarged head of the inner cannula therein with the handle grip of the enlarged head protruding out from the proximal end of the elongate housing; an inwardly facing annular ring being located within the through bore of the connector for facilitating engagement with the annular recess formed in the enlarged head of the inner cannula; and the connector supporting a locking mechanism, adjacent the distal end, for facilitating a locking engagement with the annular flange of the outer cannula, the locking mechanism comprising a pair of opposed arms located to engage with and retain the annular flange of the outer cannula whereby the connector remains continuously engaged with the outer cannula even when the inner cannula is removed from the connector, via a user grasping the protruding handle grip of the enlarged head, to replace the inner cannula.

10. The connector according to claim 9, wherein the through bore of the connector is tapered to facilitate receiving the inner cannula therein.

11. The connector according to claim 9, wherein the locking mechanism comprises a pair of opposed arms which each have a chamfered surface to facilitate receiving the annular flange of the outer cannula to facilitate a locking engagement therewith.

12. The connector according to claim 9, wherein an annular gasket is located between the distal end of the connector and the proximal end of the outer cannula to provide a sealing engagement therebetween.

13. The connector according to claim 9, wherein the connector is made from a material selected from the group comprising polypropylene, polyethylene, polycarbonate, and polyvinyl chloride.

14. The connector according to claim 9, wherein the annular ring has a slightly smaller diameter than a diameter of an annular protrusion of the inner cannula to provide an interference fit therebetween.

15. The connector according to claim 9, wherein an exterior surface of the connector has a taper to facilitate engagement with a ventilator system.

16. The connector according to claim 9, wherein the enlarged head is integrally formed with a remainder of the inner cannula to be permanently affixed thereto.

17. The connector according to claim 9, wherein the opposed flexible arms are U-shaped in transverse cross-section and a free end of each flexible arm is provided with a chamfer to facilitate receiving the annular flange of the outer cannula.

18. The connector according to claim 17, wherein a gasket is located between an end face of the outer cannula, adjacent an annular flange, and an end face of the connector, adjacent the pair of opposed flexible arms, to facilitate achieving a fluid tight seal between the connector and the outer cannula.

19. A method of attaching a connector to an outer cannula and allowing releasable attachment of an inner cannula to the connector, the method comprising the steps:

forming the inner cannula with an elongate hollow tube with an integral enlarged head attached to one end of the elongate tube, forming an annular recess on the enlarged head, forming the enlarged head of the inner cannula with a handle grip, located adjacent the proximal end, to facilitate grasping and removal of the inner cannula from the connector;

forming the outer cannula with an elongate hollow tube having a distal end and a proximal end, the proximal end of the outer cannula having an annular flange, and the elongate hollow tube of the outer cannula being sized to receive the inner cannula therein;

forming the connector as an elongate housing having a distal end and a proximal end with a through bore extending longitudinally completely therethrough from the distal end to the proximal end, the through bore being sized to receive the elongate hollow tube of the inner cannula therein with handle grip of the enlarged head protruding out from the proximal end of the elongate housing; an inwardly facing annular ring being located within the through bore of the elongate housing for facilitating engagement with the annular recess formed in the enlarged head of the inner cannula; and the connector supporting a locking mechanism, adjacent the distal end, for facilitating a locking engagement with the annular flange of the outer cannula, the locking mechanism comprising a pair of opposed flexible arms located to engage with and retain the annular flange of the outer cannula; and grasping a protruding portion of the enlarged head, when replacement of the inner cannula is desired, and withdrawing and separating the inner cannula from the connector while allowing the connector to remain continuously secured to the outer cannula.

20. The method according to claim 19 further comprising the step of replacing the inner cannula with another inner cannula after a user has used the inner cannula for a period of use of about twenty four hours.

* * * * *